(12) United States Patent
Chung et al.

(10) Patent No.: US 6,723,680 B2
(45) Date of Patent: Apr. 20, 2004

(54) COMPOSITION FOR REGULATION OF GAMETOPHYTIC SELF-INCOMPATIBILITY, CONTROL METHOD OF GAMETOPHYTIC SELF-INCOMPATIBILITY OF A PLANT AND THE PLANT SELF-POLLINATED BY USING SAID CONTROL METHOD

(75) Inventors: Il-Kyung Chung, Daegu (KR); Jong-Sang Ryu, Gyeonggi-do (KR); Myung-Hee Kim, Daegu (KR); Byung-Ju Heo, Gyeongsangbuk-do (KR); Il-Sun Chung, Gyeongsangbuk-do (KR)

(73) Assignee: Istech Co., Ltd., Gyeongsangbuk-do (KR)

( * ) Notice: Subject to any disclaimer, the term of this patent is extended or adjusted under 35 U.S.C. 154(b) by 0 days.

(21) Appl. No.: 09/959,761

(22) PCT Filed: Feb. 28, 2001

(86) PCT No.: PCT/KR01/00306

§ 371 (c)(1), (2), (4) Date: Feb. 12, 2002

(87) PCT Pub. No.: WO01/65921

PCT Pub. Date: Sep. 13, 2001

(65) Prior Publication Data

US 2003/0064894 A1 Apr. 3, 2003

(30) Foreign Application Priority Data

| Mar. 8, 2000 | (KR) | ........................................ | 2000-11550 |
| Feb. 6, 2001 | (KR) | ........................................ | 2001-05550 |

(51) Int. Cl.$^7$ ......................... A01N 59/16; A01N 59/20; A01H 1/00
(52) U.S. Cl. ........................................ 504/120; 504/187
(58) Field of Search ................................ 504/120, 187; 800/271, 273

(56) References Cited

U.S. PATENT DOCUMENTS

| 4,081,267 | A | * | 3/1978 | Hashimoto et al. | ............. | 71/93 |
| 4,090,967 | A | * | 5/1978 | Falk et al. | ...................... | 252/3 |
| 4,576,626 | A | * | 3/1986 | Bauer et al. | .................... | 71/28 |
| 5,037,959 | A | * | 8/1991 | Clarke et al. | ................. | 530/370 |
| 5,053,331 | A | | 10/1991 | Clarke et al. | ............. | 435/172.3 |
| 5,130,325 | A | * | 7/1992 | Smith | ......................... | 514/389 |
| 5,585,543 | A | | 12/1996 | Kao | ............................ | 800/205 |
| 5,628,145 | A | | 5/1997 | Beversdorf et al. | ............. | 47/58 |
| 5,821,094 | A | | 10/1998 | Rothstein et al. | ........ | 435/172.3 |
| 6,375,965 | B1 | * | 4/2002 | Matsuo et al. | ............... | 424/405 |
| 6,444,470 | B1 | * | 9/2002 | Ross et al. | .................. | 435/468 |

OTHER PUBLICATIONS

Chung et al., "Molecular Diversity of Three S–allele cDNAs Associated with Gametophytic Self–Incompatibility in *Lycopersicon Peruvianum*", Plant Molecular Biology, 1994, 26:757–762, Kluwer Academic Publishers. Printed in Belgium.

Han et al., "Pattern of Self–Incompatibility in *Paeonia Lactiflora Pallas*", Journal of Korean Breeding Science, 1997, 29(1):41–46, Only Abstract, p. 41.

Chung et al., "An S Rnase Gene of *Lycopersicon Peruvianum* L. is Highly Expressed in Transgenic Tobacco but Does Not Affect Self–Incompatibility", Journal of Plan, 1999, 154:63–70, Urban & Fischer.

Nakata et al., "Construction and Some Characterization of a Yeast Artificial Chromosome Library from DNA Of a Tomato Line Having Four Disease Resistance Traits", Biosci. Biotech. Biochem., 1993, 57(10):1790–1792, Dept. of Agricultural Chemistry, Univ. of Tokyo.

Chung et al., "The 5' Flanking Sequences of Two S Alleles in Lycopersicon Peruvianum Are Highly Heterologous but Contain Short Blocks of Homologous Sequences", Plant Cell Physiol., 1995, 36(8):1621–1627, JSPP.

Itsukyon et al., "S–Ribonuclease Gene and Promoter Sequence", Japanese Patent No. 7–187557, 1995, Only Abstract.

Jahnen et al., "Inhibition of in Vitro Pollen Tube Growth by Isolated S–Glycoproteins of *Nicotiana Alata*", Plant Cell, 1989. 1:501–510, American Society of Plant Physiologists.

Singh et al., "Characterization of Ribonuclease Activity of Three S–Allele–Associated Proteins of *Petunia Inflata*", Plant Physiology, 1991, 96:61–68.

Huang et al., "Ribonuclease Activity of Petunia Inflata S Proteins is Essential for Rejection of Self–Pollen", Plant Cell, 1994, 6:1021–1028, American Society of Plant Physiologists.

Daphner et al., "Self–Incompatibility Alleles of Brassica", WO9318149, 1993, Only Abstract.

Steven et al., "S–Locus Receptor Kinase Gene in a Self–Incompatible Brassica Napus Line", WO9409139, 1994, Only Abstract.

* cited by examiner

*Primary Examiner*—S. Mark Clardy
(74) *Attorney, Agent, or Firm*—Foley & Lardner

(57) ABSTRACT

The present invention relates to a regulation composition for gametophytic self-incompatibility which contains sulfates especially $CuSO_4$ and $ZnSO_4$ as an inhibitor, which prevents a style-specific RNase activity regulating gametophytic self-incompatibility; a control method for gametophytic self-incompatibility of a plant by using the regulation composition for gametophytic self-incompatibility; and a plant self-pollinated by destroying the gametophytic self-incompatibility, using the control method.

By using the regulation composition for gametophytic self-incompatibility according to the present invention, a single species of fruit trees can be self-pollinated without cultivating other pollinizer, so that fruition rate can be increased and the productivity per unit area can be maximized.

10 Claims, 9 Drawing Sheets

COMPOSITION FOR REGULATION OF GAMETOPHYTIC SELF-INCOMPATIBILITY, CONTROL METHOD OF GAMETOPHYTIC SELF-INCOMPATIBILITY OF A PLANT AND THE PLANT SELF-POLLINATED BY USING SAID CONTROL METHOD

This application has been filed under 35USC 371 as the national stage of international application PCT/KR01/00306, filed Feb. 28, 2001.

TECHNICAL FIELD

The present invention relates to a regulation composition for gametophytic self-incompatibility, a control method for gametophytic self-incompatibility and a plant self-pollinated by using the control method. More particularly, the present invention relates to a regulation composition for gametophytic self-incompatibility containing sulfates, especially $CuSO_4$ and $ZnSO_4$, as an inhibitor that prevents a style-specific RNase activity regulating gametophytic self-incompatibility; a control method for gametophytic self-incompatibility of plants by using the regulation composition for gametophytic self-incompatibility; and a plant self-pollinated of which gametophytic self-incompatibility is destroyed by using the control method.

BACKGROUND ART

Over half of the flowering plants in this world have gametophytic self-incompatibility. The gametophytic self-incompatibility means the property that is not self-pollinated. Therefore, the gametophytic self-incompatible plants can be pollinated only by genetically different pollen. So, such plants can only bloom without any fruition in case that there is only one species.

On the other hand, natural pollination between plants belonging to different species is mediated by pollinators such as honeybee and drone fly, or by wind. However, pollinators are decreasing suddenly in recent years due to environmental pollution according to the excess use of agricultural chemicals and rapid industrialization. Although the number of pollinators and pollinizers is sufficient, it is difficult to achieve the stable rate of fruitions in case that the working of pollinators is disturbed by the hindrance factor of weather conditions such as low temperature, strong wind, and rain fall, which appear in blooming season every year.

Furthermore, the rate of natural fruition in the farm house cultivating only one species of crop for high profit gets to further decrease because pollinizers are insufficient.

Therefore, since it is difficult to acquire both fruition stability of crops and good quality of fruits under the condition of natural pollination, in recent years artificial pollination using imported pollens has been carried out, or a method that releases pollinators such as artificially bleeded *Osmia ocrnifrons* which is imported from foreign countries in blooming season has been used. Especially, in artificial pollination method, pollens of different pollinizers are smeared on the stigma of style by human, not by pollinators. So it is not economical because it needs many labor and high costs.

In natural fruit trees, flowering plants, medicinal plants, and vegetables of eggplant family, a style-specific RNase is secreted from a pistil, the reproductive organ RNase having the different genetic phenotype according to the species exists in a style. The mechanism is as follows. A style-specific RNase is secreted when self-pollen tube elongates from a style of a pistil to an ovary, and degrades only rRNA of self-pollen selectively (McClure et al, *Nature,* 1991). By the mechanism, the pollen tube doesn't elongate to the ovary, that is, the elongation of pollen tube is destroyed at a specific site, ⅓ point of a pistil, and finally fruition cannot be produced as a result of being unable to accomplish pollinatioin by self-pollen.

Furthermore, according to the research up to now, the RNase secreted from a style enters into self- or nonself-pollen unselectively, but the RNase binds to an inhibitor or a receptor within self-pollen which react with the RNase specifically. It is speculated that this reaction is related to the signal transduction pathway degrading rRNA of self-pollen selectively, and the pollination cannot be accomplished because self-pollen tube is destroyed before it reaches to the ovary in case of self-pollen.

On the other hand, nonself-pollen, which is originated from pollinizer having different genetic phenotype transferred by pollinators or wind, can elongate the pollen tube normally. This phenomenon is illustrated by the hypothesis according to the research up to now. The hypothesis is as follows. Since the structure of the receptor that binds with RNase secreted from a pistil which exists in the pollen of different phenotype, is not identical to that of the receptor of its own phenotype, signal transduction pathways are not progressed thereinafter. As a result, RNase does not attack rRNA of nonself-pollen, and the elongation of pollen tube is induced normally so that pollination can be achieved finally.

Though many researchers in the world keep studying an inhibitor or a receptor molecule of pollen now, however, they have not found clear clue about that. It was only reported that RNase secreted from a style was found in the elongation tissue of pollen tube by observing through the microscopic and immunological method.

Furthermore, it has been reported that gametophytic self-incompatibility of fruit trees like apple, pear, coffee and almond as well as some flowering plants, medicinal plants and eggplant family like wild-type tomato, eggplant, tobacco and potato, is regulated by pistil(style) and gene-specific RNase (Il-Kyung, Chung et al., *Plant Molecular Biology,* 26:757–762, 1994; Il-Kyung, Chung et al., *Journal of Korean Breeding Science,* 29(1):41–46, 1997; Il-Kyung, Chung et al., *Journal of Plant Physiology,* 154:63–70, 1999).

In relation to the report, the present inventor previously reported a style-specific RNase isolated from wild-type tomatoes in 1992 (Il-Kyung, Chung et al., *Bioscience Biotechnology Biochemistry* 57(7):1172–1176, 1993; Japanese patent application No. 1,262,865). Also the present inventor identified a gene related to gametophytic self-incompatibility of plants like tomato and *Lillop Koreana Kakai* (Il-Kyung, Chung et al., *Plant Molecular Biology,* 26:757–762, 1994; Il-Kyung, Chung et al., Plant Cell Physiology, 36(8):1621–1627, 1995; Japanese Patent No. 7-187557).

To overcome the problem of the gametophytic self-incompatible plants, the present inventor identified an inhibitor preventing a style-specific RNase activity, provided a control method for gametophytic self-incompatibility by using the inhibitor and a plant self-pollinated, and suggested a new agricultural method that is very economical as well as ensures good quality of fruits by manipulating plants of fruit trees to be pollinated or producing fruits by self-pollen.

DISCLOSURE OF THE INVENTION

The object of the present invention is to provide a regulation composition for gametophytic self-incompatibility containing an inhibitor, which prevents a style-specific RNase regulating gametophytic self-incompatibility.

Another object of the present invention is to provide a control method for gametophytic self-incompatibility by using the regulation composition.

Also the object of the present invention is to provide a plant self-pollinated in which gametophytic self-incompatibility is destroyed.

Hereinafter, the present invention is described in detail.

The present invention provides a regulation composition for gametophytic self-incompatibility which includes inhibitor inhibiting a style-specific RNase activity regulating gametophytic self-incompatibility.

The present inventor has tried to induce pollination by self-pollen by controlling gametophytic self-incompatibility of plants existing in the natural world, by finding out the style-specific RNase inhibitor related to gametophytic self-incompatibility.

First of all, the present inventor isolated and purified RNase from the style, the reproductive organ of Fuji apple, which plays a critical role in causing gametophytic self-incompatibility (see table 2). Afterwards, the present inventor isolated RNase respectively from a root, leaf, stalk, petal and calyx of Fuji apple, and electrophoresed the said RNases with the RNase isolated from a style of Fuji apple. Hence, the present inventor confirmed that RNase isolated from a style is a style-specific RNase by RNase activity staining (see FIG. 1). Furthermore, to investigate the difference between style-specific RNases according to species, the present inventor isolated and purified RNase from the style of Hongro, Hongok, Fuji, Gookwang and Sgaroo, and then, performed RNase activity staining and silver staining. As a result, it was confirmed that style-specific RNases are different according to species of apple (see FIG. 2).

To confirm the style-specific RNase of the Fuji apple controls gametophytic self-incompatibility, the present inventor observed the elongation pattern of pollen tube of Fuji apple by adding the style-specific RNase to the medium for pollen tube elongation (William Jahnen et al., *Plant Cell*, (1):501–510, 1989; Harris et al., *Plant Physiology*, 189:360–367, 1989), which can induce the elongation of pollen tube from pollen artificially (see FIG. 3).

From the result, it can be confirmed that a style-specific RNase controls gametophytic self-incompatibility by inhibiting the elongation of pollen tube.

The present inventor observed the elongation patterns of pollen tube of Fuji apple by adding a style-specific RNase of Fuji apple and various chemicals to the medium for pollen tube elongation, and by using the creative experimental method provided in the present invention (See FIGS. 4 and 5). As a result, RNase activity inhibiting the elongation of pollen tube was inhibited effectively by a sulfate and the pollen tube elongated normally. From the result, it is confirmed that metal ion-bound sulfate is an inhibitor of the RNase. Hence, the sulfate functions as a regulation composition for gametophytic self-incompatibility, particularly, among sulfates, $CuSO_4$, $MgSO_4$, $ZnSO_4$ and $MnSO_4$ are preferred to the regulation composition for gametophytic self-incompatibility, and $CuSO_4$ and $ZnSO_4$ are more preferable.

Further, the present invention provides a control method for gametophytic self-incompatibility by using the regulation composition for gametophytic self-incompatibility.

Upon the basis of the experimental results performed by using the medium for pollen tube elongation, the present inventor put into practice the inhibition effect of gametophytic self-incompatibility by regulation composition for gametophytic self-incompatibility of the present invention in wild-type tomato and Fuji apple, which are gametophytic self-incompatible crop growing in the practical cultivation environment.

First of all, to determine the period of treating the regulation composition for gametophytic self-incompatibility of the present invention, the present inventor treated wild-type tomato with 1 mM $CuSO_4$ and $ZnSO_4$ from 7 days before blooming to 2 days after full blooming, and Fuji apple with 1 mM $CuSO_4$ and $ZnSO_4$ from 5 days before blooming to 2 days after full blooming to investigate the rate of self-pollination. When wild-type tomato was treated with the regulation composition for gametophytic self-incompatibility of the present invention at the early blooming period, from 7 days before blooming to 4 days before blooming, the fruition rate was over 70%. And when Fuji apple was treated with the regulation composition for gametophytic self-incompatibility of the present invention at the early blooming period, from 5 days before blooming to 3 days before blooming, the fruition rate was also over 70%. Therefore, gametophytic self-incompatibility in plants can be controlled by the method of spraying the regulation composition for gametophytic self-incompatibility including an inhibitor of style-specific RNase activities during a specific period of plant growth, and it is preferred that treatment period of the regulation composition for gametophytic self-incompatibility is from budding formation period, a specific period of plant growth to the early blooming period, before full blooming.

Moreover, to investigate preferable concentration of treatment of the regulation composition for gametophytic self-incompatibility of the present invention, 0 or 1,500 ppm $CuSO_4$ and $ZnSO_4$ were treated to wild-type tomato and Fuji apple at the early blooming period and the harmful effects of a medicine and fruition rates were investigated (see FIGS. 6 and 7). Since absorption rate of the regulation composition for gametophytic self-incompatibility of the present invention can be increased by treating it with a spreader in cultivating fruit trees, the $CuSO_4$ and $ZnSO_4$ were treated with a spreader by a method of spraying on the fruit trees at a specific period, that is, the early blooming period.

Thus, it was shown that fruits and plants that are pollinated by self-pollen could be acquired by the treatment of a specific concentration of $CuSO_4$ and $ZnSO_4$ in wild-type tomato and Fuji apple without harmful effects of the medicine. From the results, it can be concluded that an inhibitor composition of a style-specific RNase of the present invention is effective in inhibition of a style-specific RNase without respect to species, and preferable concentration of $CuSO_4$, which is treated at the early blooming period, is at 100~700 ppm and preferable concentration of $ZnSO_4$ is at 100~800 ppm. Furthermore, very high pollination rate, without harmful effects of a medicine, could be achieved by spraying the inhibitor composition for gametophytic self-incompatibility of the present invention, which was mixed with the desirable amount of spreader according to the manufacturers' instruction. Among the spreaders, the spreader of hexaconazole class, siloxane class and alkylaryl polyethoxylate class is preferable to achieve high fruition rate.

The preferable concentration of the inhibitor composition for gametophytic self-incompatibility of the present invention was shown in table 1.

TABLE 1

Appropriate concentration of effective components of inhibitor composition of a style-specific RNase

| concentration | effective component | |
| --- | --- | --- |
| | $CuSO_4$ | $ZnSO_4$ |
| the lowest concentration showing inhibiting effect (ppm) | 100 | 100 |

TABLE 1-continued

Appropriate concentration of effective components
of inhibitor composition of a style-specific RNase

| concentration | effective component | |
|---|---|---|
| | $CuSO_4$ | $ZnSO_4$ |
| the highest concentration not showing harmful effects of a medicine (ppm) | 700 | 800 |

When $CuSO_4$ is used as an effective component of the style-specific RNase inhibitor as shown in the table 1, if the concentration of $CuSO_4$ is below 100 ppm, it is difficult to achieve a stable fruition rate over 70% because it cannot inhibit RNase activity appropriately, on the other hand, if the concentration of CuSO4 is over 700 ppm, it is not economical because it can induce harmful effects of a medicine. Furthermore, when $ZnSO_4$ is used as an effective component of the style-specific RNase inhibitor, if the concentration of $ZnSO_4$ is below 100 ppm, it is difficult to achieve a stable fruition rate over 70% because it cannot inhibit RNase activity appropriately, on the other hand, if the concentration of $ZnSO_4$ is over 800 ppm, it is not economical because it can induce harmful effects of a medicine.

Moreover, the present invention provides a plant self-pollinated by destroying the gametophytic self-incompatibility using the control method.

As the results mentioned above, a self-pollinated plant in which gametophytic self-incompatibility is destroyed can be acquired by using the regulation composition for gametophytic self-incompatibility of the present invention. In examples of plants which can be applied to the control method for gametophytic self-incompatibility of the present invention, there are fruit trees such as apple, pear, coffee and almond; flowering plants; medicinal plants; and vegetables of eggplant family such as tomatoes, eggplants, tobaccos and potatoes in addition to Fuji apple and wild-type tomato, which were used in the preferred embodiment of the present invention.

→: a band showing a style-specific RNase activity

| Lane 1: root | Lane 2: leaf |
|---|---|
| Lane 3: stalk | Lane 4: petal |
| Lane 5: calyx | Lane 6: style |

Figure 2:
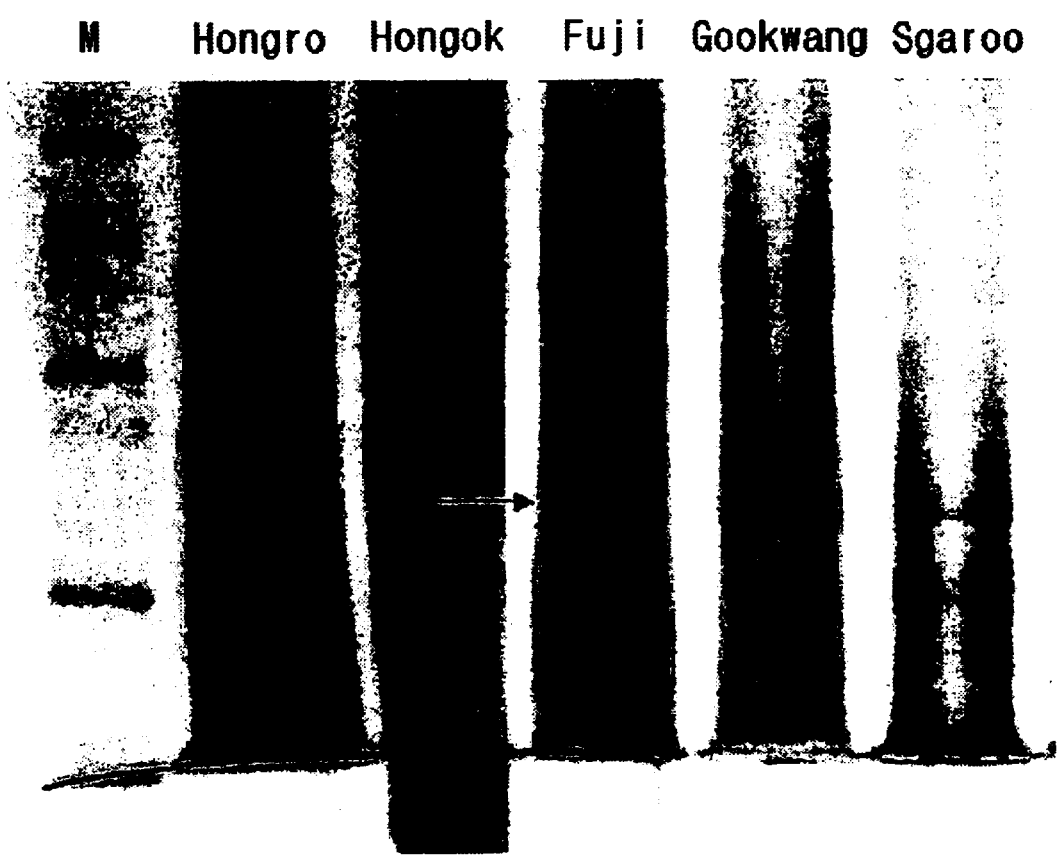

FIG. 2 shows the result of silver staining of the total protein extract isolated from the style of Hongro, Hongok, Fuji, Gookwang and Sgaroo, which are agricultural apple species.

→: a band showing a genetic phenotype-specific RNase activity of Fuji apple

M: Standard Molecular Marker

| Lane 1: Hongro | Lane 2: Hongok |
|---|---|
| Lane 3: Fuji | Lane 4: Gookwang |
| Lane 5: Sgaroo | |

Figure 3:
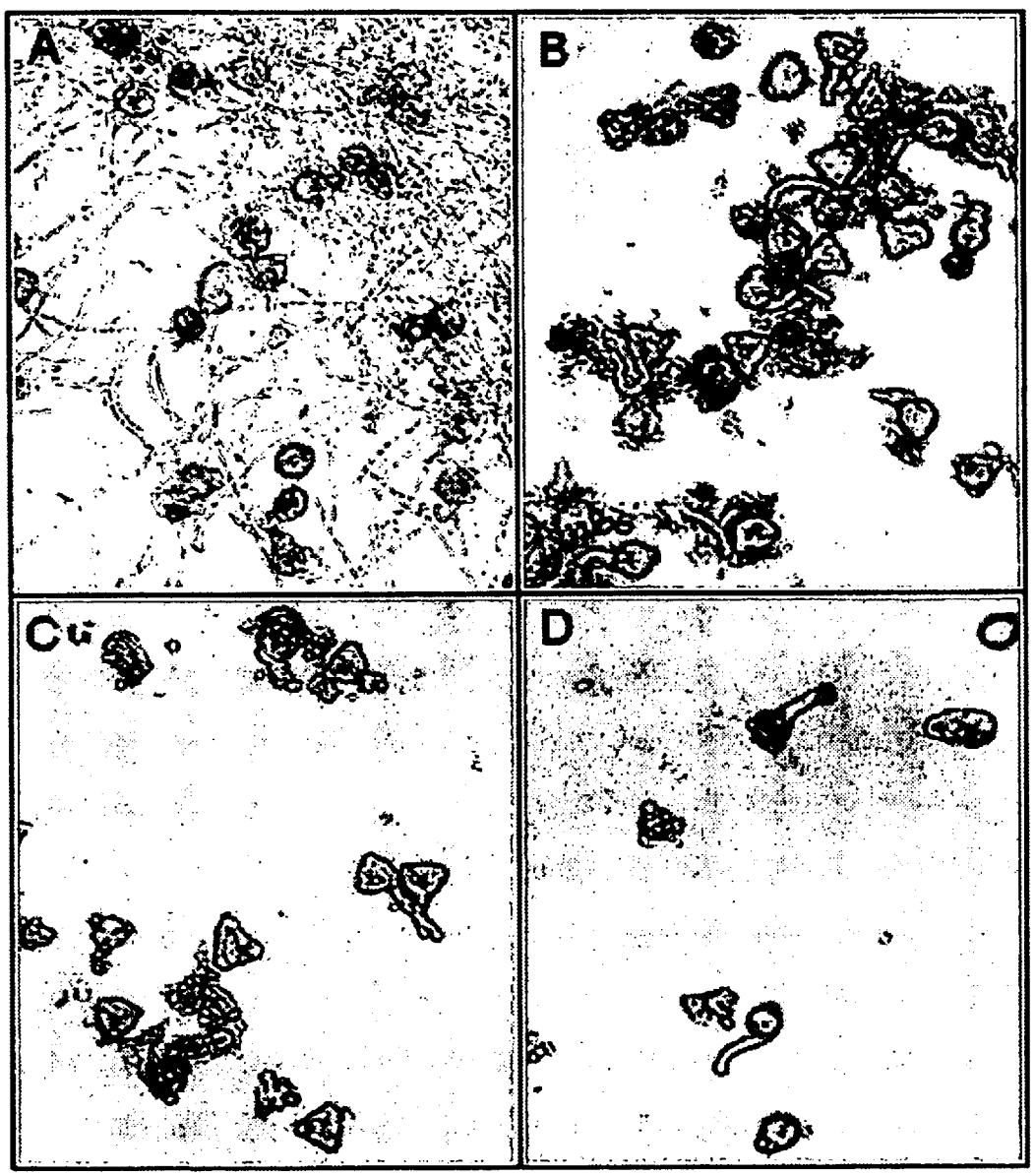

FIG. 3 represents microscopic photography showing the result that the elongation of pollen tube of Fuji apple is inhibited in the medium for pollen tube elongation including style-specific RNase.

Figure 4:
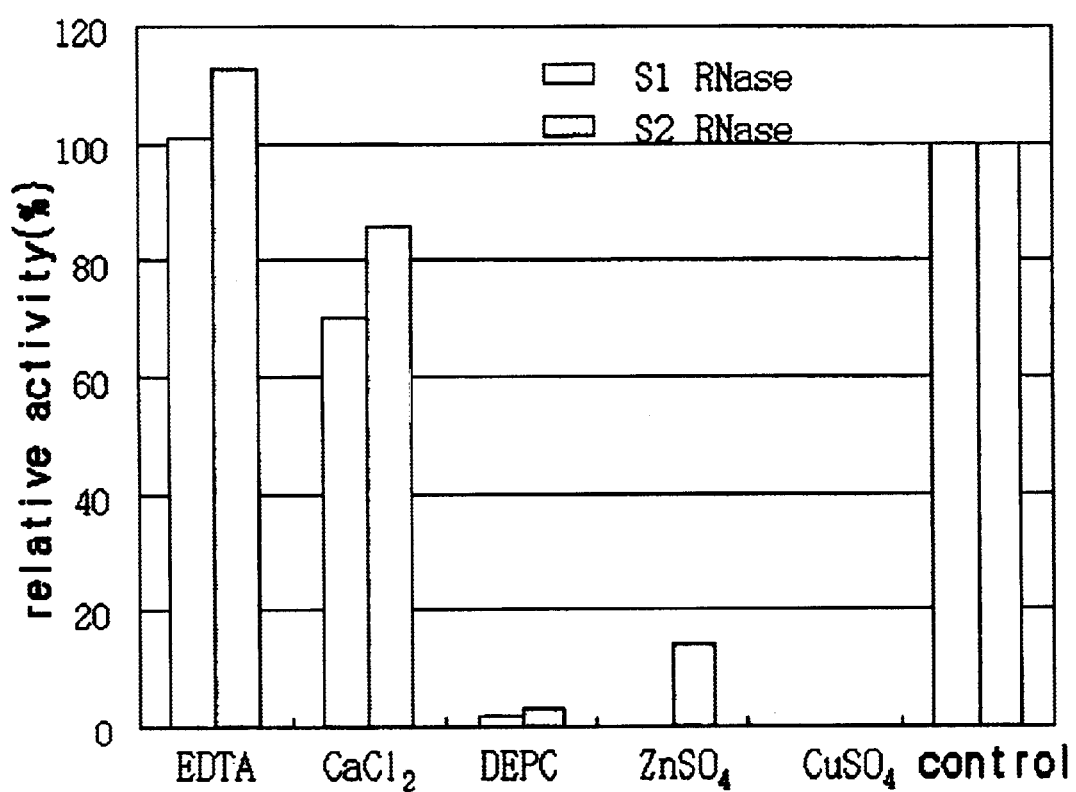

A: No addition of RNase   B: addition of 2 units of RNase
C: addition of 4 units of RNase   D: addition of 6 units of RNase FIG. 4 represents a graph showing the inhibition degrees of chemical components inhibiting style-specific S1 and S2 RNase activities, which are isolated and purified from the style of Fuji apple.

Figure 5:
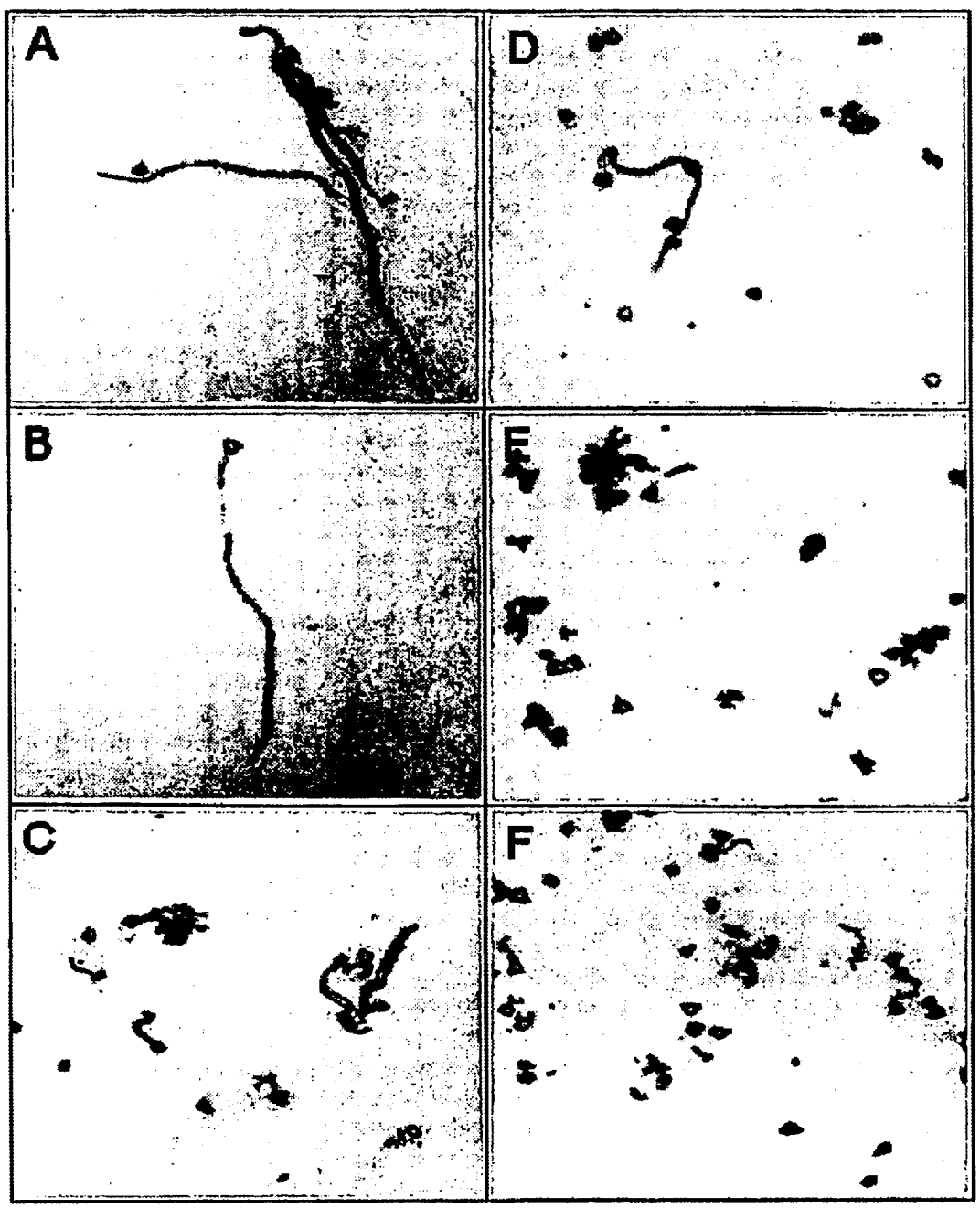

FIG. 5 represents microscopic photography showing the result that the pollen tube of Fuji apple elongates in the medium for pollen tube elongation containing a style-specific RNase and inhibitor composition thereof.

Figure 6A:

A: addition of 1 mM $ZnSO_4$ and 10 units of RNase
B: addition of 2 mM $ZnSO_4$ and 10 units of RNase
C: addition of 5 mM $ZnSO_4$ and 10 units of RNase
D: addition of 1 mM $CuSO_4$ and 10 units of RNase
E: addition of 2 mM $CuSO_4$ and 10 units of RNase
F: addition of 5 mM $CuSO_4$ and 10 units of RNase FIG. 6a is a picture showing wild-type tomato at the early blooming period before it is treated with a style-specific RNase inhibitor composition of the present invention.

Figure 6B:

FIG. 6b is a picture showing wild-type tomato pollinated by self-pollen by destroying the garnetophytic self-incompatibility after it is treated with a style-specific RNase inhibitor composition of the present invention.

Figure 7A:

FIG. 7a is a picture showing Fuji apple at the early blooming period before it is treated with a style-specific RNase inhibitor composition of the present invention.

Figure 7B:

FIG. 7b is a picture showing Fuji apple pollinated by self-pollen by destroying the gametophytic self-incompatibility after it is treated with a style-specific RNase inhibitor composition of the present invention.

BEST MODE FOR CARRYING OUT THE INVENTION

The present invention is more specifically illustrated by the following examples.

However, it should be understood that these examples are provided only for illustration of the present invention, but not intended to limit the present invention in any manner.

EXAMPLE 1

Isolation and Purification of a Style-Specific RNase, a Control Protein for Gametophytic Self-Incompatibility <1-1> Isolation and Purification of RNase from each Organ of Fuji Apple To isolate RNase from a style, root, leaf, stalk, petal and calyx of Fuji apple, experiment was conducted as follows.

Buffer solution containing 10 mM $Na_2PO_4$ (pH 6.0), 10 mM EDTA, 1 mM PMSF and 1% (w/v) polyvinyl pyrrodine was added to 1 g of the style of Fuji apple and total protein was extracted by homogenizing with a mortar. The extracted total protein was concentrated with 40% ammonium sulfate, and then, dialyzed in 5 mM $Na_2PO_4$ buffer solution by using half permeable membrane (molecular cut-off: 12,000 Da). As a result, the fraction with strong RNase activity was obtained, and total RNase activities were 295,000 units.

Gel filtration chromatography using column filled with Bio-gel P-60 (Bio-Rad, Englang) resin was performed with the fractions having strong RNase activity (Harris et al.,

*Plant Physiology*, 89:360–367, 1989; Anuradha Singh et al., *Plant Physiology*, 96:61–68, 1991; Shihshie et al., *Plant Cell,* 6:1021–1028, 1994). 500 μl of the fractions with strong RNase activity were loaded and adsorbed to the column by the speed of 1.5 cm/hr at 4° C., and eluted with buffer containing 0.5 M NaCl and 50 mM $Na_2PO_4$ under the same condition. As the result of the gel filtration chromatography, 1,282,000 units of RNase that is expressed specifically in a style and has the molecular weight of 23~25 kDa, was collected.

Furthermore, 20~30 kDa of RNases in molecular weight were isolated and purified from a root, leaf, stalk, petal and calyx of Fuji apple respectively, according to the same method mentioned above.

<1-2> Activity Staining of RNase Isolated and Purified from each Organ of Fuji Apple To investigate organ-specificity of RNase expressed in each organ of Fuji apple, RNases of each organ isolated and purified in the example 1-1, were electrophoresed on 15% polyacrylamide gel at 4° C. The electrophoresed gel was soaked in 0.1 M Tris-HCl (pH 7.4) buffer. Enzyme reaction was performed adding 300 μg/ml of ribosomal RNA of yeast (Sigma, USA) as a substrate at 37° C. for 120 minutes.

Figure 1:
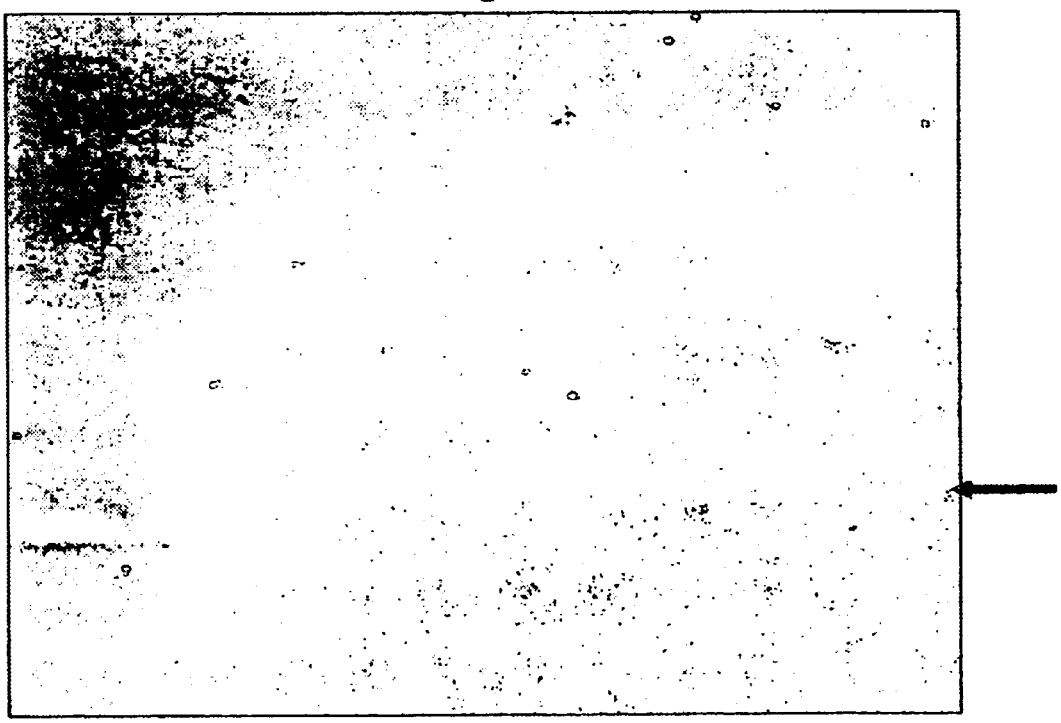
FIG. 1 shows the result of activity staining of RNase which is isolated from the root, leaf, stalk, petal, calyx and style of Fuji apple and degrades ribosomal RNA of yeast.

From the result of activity staining in FIG. 1, it was confirmed that the RNases of a style, root, leaf, stalk, petal and calyx had different molecular weight according to organ, and the RNase isolated from a style was a style-specific RNase.

<1-3> Investigation of a Style-Specific RNase According to Apple Species

To investigate whether a type of a style-specific RNase is different according to apple species, the RNases were isolated and purified from Hongro, Hongok, Fuji, Gookwang and Sgaroo, which are agricultural species, according to the method of the example 1-1, and the RNase activity staining and silver staining were performed as follows.

RNase activity staining, which was isolated and purified from each species, was performed according to the method of the example 1-2. Also, the RNase was electrophoresed on 15% polyacrylamide gel, and silver staining (Giulian G. G. et at., *Anal. Biochem.,* 129, 1983) was performed. The result was shown in FIG. 2.

From the result, it is conformed that a style-specific RNase having different molecular weight according to apple species exists, and genetic phenotype-specific RNase is expressed in pollinizer and fruit trees accepting pollens from the pollinizer.

<1-4> Purification for High Degree of Purity of a Style-Specific RNase

To purify a style-specific RNase of Fuji apple isolated and purified in the example 1-1 with high degree of purity, experiment was conducted as follows.

The style-specific RNase was concentrated with Centricon-10 (Millipore), and purified with high degree of purity by performing ion-exchange chromatography using Mono-S column (Amersham Pharmacia) and FPLC system (Bio-Rad). The protein adsorbed to the column was eluted by using buffer containing 0.5 M NaCl and 50 mM $Na_2PO_4$ (pH 6.0) with the speed of 1.0 ml/min.

As a result, two kinds of S1 RNase and S2 RNase fractions with strong activities were collected. This is because two kinds of style-specific RNase exist in Fuji apple, a fruit tree of agricultural species, as a heterozygote genetically. Hence, the collected RNases have different molecular weight, isoelectric point and purification profiles as shown in Table 2 (S: Self-incompatibility).

TABLE 2

Profile of enzyme activity on each purification step of a style-specific RNase

| | total protein (μg/μl) | total activity[a] (unit) | specific activity[b] (unit) | efficiency (%) |
|---|---|---|---|---|
| total protein extract | 7.52 | 1,282,000 | 34.10 | 100 |
| 40% ammonium sulfate | 1.25 | 295,000 | 157.33 | 22 |
| Biogel P-60 gel filtration | 0.047 | 10,350 | 880.85 | 18 |
| FPLC (Mono S) | | | | |
| S1 | 0.016 | 136 | 8,500 | 10 |
| S2 | 0.019 | 114 | 6,000 | 14 |

[a]sum of activity to the amount of total protein (total protein × unit)
[b]value of the total activity divided by total protein (total activity ÷ total protein)

As shown in Table 2, total enzyme activity of S1 RNase and S2 RNase was 136 units and 114 units respectively. Likewise, specific activity of S1 RNase and S2 RNase was 8,500 nits and 6,000 units respectively. The purification efficiency of S1 RNase and S2 RNase was 10% and 14% respectively when assuming total protein extract as 100%. From these results, it is noticed that a style-specific RNase of Fuji apple was purified with a high degree of purity.

EXAMPLE 2

Inhibition of Pollen Tube Elongation of Self-Pollen by a Style-Specific RNase of Fuji To investigate the effect of the style-specific S1 RNase purified in the example 1-4 on pollen tube elongation of self-pollen, experiment was conducted as follows. First of all, only the self-pollen made from a stamen of Fuji apple was isolated. The isolated pollen was cultured in the medium for pollen tube elongation, which was added with 0, 2, 4 and 6 units ($mg^{-1}min^{-1}ml$) of S1 RNase purified in the example 1-4, respectively, in a dark condition for 24 hours at 28° C. The medium for pollen tube elongation is composed of 20 mM Mes-KOH (pH 6.0), 0.07% $Ca(NO_3)_2·4H_2O$, 0.02% $MgSO_4·7H_2O$, 0.01% $KNO_3$, 0.01% $H_3BO_3$ and 2% sucrose, and elongates pollen tube artificially.

The experimental result of the elongation patterns of pollen tube is shown in FIG. 3. As shown in FIG. 3, the pollen tube elongation of self-pollen was inhibited when 2, 4 and 6 units (B, C and D) of a style-specific S1 RNase was added in comparison with control (A) to which a style-specific S1 RNase was not added. From the results, it was confirmed that determinant that induces gametophytic self-incompatibility was a style-specific RNase.

EXAMPLE 3

Investigation of a Style-Specific RNase Inhibitor

The activity variation of the style-specific S1 RNase and S2 RNase purified in the Example 1-4 was investigated by adding chemicals acting as an inhibitor of protein degradation enzyme. RNase activity was measured by adding general stimulators of RNase activity, inhibitors of RNase activity commercially available and inhibitor candidate of a style-specific RNase of the present invention (Singh A. et al., *Plant Physiology,* 96:61–68, 1991). Among them, 1 mM EDTA, which is a representative inhibitor of protein degradation enzyme, 1 mM $CaCl_2$, a stimulator of RNase activity, 1 mM DEPC (Sigma), a fatally poisonous inhibitor of RNase activity commercially available, and 1 mM $ZnSO_4$ and 1 mM CuSO$_4$, inhibitor candidates of the style-specific RNase was added respectively to mesure RNase activity. The result is shown in FIG. 4.

As a result, the style-specific RNase activity was remarkably inhibited below 15% when 1 mM (about 288 ppm) ZnSO$_4$ and 1 mM (about 250 ppm) CuSO$_4$ were added respectively, in comparison with the control having 100% RNase activity in phosphate buffer. Inhibitors of RNase activity such as DEPC, also inhibited the style-specific RNase activity, however, they are restricted for crops because they are fatally poisonous material. From these results, it was proven that ZnSO$_4$ and CuSO$_4$ are effective inhibitor of a style-specific RNase activity.

EXAMPLE 4

Pollen Tube Elongation of Self-Pollen by the Treatment of a Style-Specific RNase Inhibitor To investigate the effect of ZnSO$_4$ and CuSO$_4$, which were proved to be a style-specific RNase inhibitor in the Example 3, on the pollen tube elongation of self-pollen, the experiment was conducted as follows. 10 units (mg$^{-1}$min$^{-1}$ml$^{-1}$) of the style-specific S1 RNase was added to the medium for pollen tube elongation, and ZnSO$_4$ and CuSO$_4$ were added thereto at 1 mM, 2 mM and 5 mM respectively. And then, pollen tube was cultured according to the same method as the Example 2.

From the results of elongation patterns of pollen tube, as shown in FIG. 5, it was observed that RNase activity inhibiting the elongation of pollen tube was overcome by adding 1 mM ZnSO$_4$, 2 mM ZnSO$_4$ and 1 mM CuSO$_4$, and the pollen tube elongated again. From these results, it was confirmed that ZnSO$_4$ and CuSO$_4$ were effective inhibitors of a style-specific RNase activity.

EXAMPLE 5

Determination of the Period of Treating a Style-Specific RNase Inhibitor in Wild-Type Tomato and Investigation of Fruition Rate and its Harmful Effects of a Medicine <5-1> Determination of the Period of Treating a Style-Specific RNase Inhibitor To test the effect of a style-specific RNase inhibitor in a practical cultivating environment, the style-specific RNase of the present invention was treated to the wild-type tomato that was cultivated in a greenhouse for research (located in Taegu Catholic University, Kyungsan city, Kyungsangpukdo, Republic of korea). In the present invention, the experiment was performed under the environmental condition that can keep the wild-type tomato, a representative plant having gametophytic self-incompatibility, a single species genetically.

To determine the treatment period of a style-specific RNase inhibitor, the inhibitor was treated at the early blooming period (budding formation period~prior to fill blooming), the middle blooming period (full blooming) and the late blooming period (1 day after full blooming~falling period of petal) respectively. The inhibitors, ZnSO$_4$ and CuSO$_4$ were then added with 1 mM (about 288 ppm) and 1 mM (about 250 ppm) respectively at 9~11 a.m., when pollination of plant occurs most actively. Fruition rate was investigated, and the results of 4 times repeated experiments for 25 blooming periods (reproductive organ containing a stamen, a stigma, a petal, etc.) in each experiment were shown in Table 3 with the statistic value.

TABLE 3

Fruition rate of wild-type tomato treated with a style-specific inhibitor, according to each blooming period

| Blooming period | Fruition rate at 1 mM ZnSO$_4$ treatment | Fruition rate at 1 mM CuSO$_4$ treatment |
| --- | --- | --- |
| The early period | | |
| 7 days before blooming | >92% | >91% |
| 6 days before blooming | >90% | >91% |
| 5 days before blooming | >83% | >86% |
| 4 days before blooming | >71% | >74% |
| 3 days before blooming | >30% | >37% |
| 2 days before blooming | 0 | 0 |
| 1 day before blooming | 0 | 0 |
| The middle period | | |
| Full blooming | 0 | 0 |
| The late period | | |
| 1 day after full blooming | 0 | 0 |
| 2 days after full blooming | 0 | 0 |

As shown in Table 3, it was confirmed that it is possible to achieve fruition rate over 70% when a style-specific RNase inhibitor was treated at the early blooming period (4 days~7 days before full blooming)

<5-2> Investigation of Fruition Rate and the Harmful Effects of a Medicine According to Concentration of a Style-Specific RNase Inhibitor To investigate the fruition rate and harmful effects of a medicine according to the concentration of style-specific RNase inhibitors, ZnSO$_4$ and CuSO$_4$, style-specific RNase inhibitors of the present invention, were treated to wild-type tomato with various concentration in 4 days before full blooming.

Furthermore, to maximize the efficiency of the style-specific RNase inhibitor of the present invention as fruition control agents, ZnSO$_4$ or CuSO$_4$ was mixed with spreader of hexaconazole, siloxane and alkylaryl polyethoxylate class according to most appropriate usage amount by the manufacturer, and treated.

TABLE 4

Investigation of fruition rate and harmful effects of a medicine to wild-type tomato according to the concentration variation of a style-specific RNase inhibitor

| | Effective component | | | |
| --- | --- | --- | --- | --- |
| | Fruition rate and harmful effects of medicine according to the concentration variation of ZnSO$_4$ | | Fruition rate and harmful effects of medicine according to the concentration variation of CuSO$_4$ | |
| Concentration (ppm) | Fruition rate (%) | Harmful effects of a medicine | Fruition rate (%) | Harmful effects of a medicine |
| 0 | 0 | no | 0 | no |
| 20 | 0 | no | 0 | no |

TABLE 4-continued

Investigation of fruition rate and harmful effects of a medicine to wild-type tomato according to the concentration variation of a style-specific RNase inhibitor

| | Effective component | | | |
|---|---|---|---|---|
| | Fruition rate and harmful effects of medicine according to the concentration variation of $ZnSO_4$ | | Fruition rate and harmful effects of medicine according to the concentration variation of $CuSO_4$ | |
| Concentration (ppm) | Fruition rate (%) | Harmful effects of a medicine | Fruition rate (%) | Harmful effects of a medicine |
| 40 | 13 | no | 15 | no |
| 60 | 31 | no | 41 | no |
| 80 | 61 | no | 59 | no |
| 100 | 99 | no | 97 | no |
| 200 | 98 | no | 92 | no |
| 300 | 93 | no | 88 | no |
| 400 | 88 | no | 85 | no |
| 500 | 85 | no | 77 | no |
| 600 | 84 | no | 73 | no |
| 700 | 74 | no | 73 | no |
| 800 | 71 | no | 44 | Little |
| 900 | 62 | Weak | 16 | Little |
| 1000 | 0 | Little | 7 | Little |
| 1100 | 0 | Little | 0 | Little |
| 1200 | 0 | Little | 0 | Excessive |
| 1300 | 0 | Excessive | 0 | Excessive |
| 1400 | 0 | Excessive | 0 | Excessive |
| 1500 | 0 | Excessive | 0 | Excessive |

A composition mixed with the spreader of siloxane class (brand name:silhouette, Dongbu precision chemical company, Korea) to 0.0335% was prepared and the composition was treated to wild-type tomato. And then, fruition rate by self-pollen was investigated, as shown in Table 4. The experimental results of 4 times repeated experiments for 25 blooming periods were showed as the statistical value.

In case of $ZnSO_4$, the fruition rate by self-pollen was achieved over 70%, if fruition rate is set 100% as standard when pollination was performed in the range of 100~800 ppm at all the blooming periods. In the concentration of 900 ppm over, harmful effect of a medicine occurred like the colors of flower petal changed to yellow or the flower petal fell an early stage. In case of $CuSO_4$, the fruition rate by self-pollen was achieved over 70%, if fruition rate is set 100% as standard when pollination was performed in the range of 100~700 ppm at all the blooming periods. In the concentration of 800 ppm over, harmful effect of a medicine occurred.

EXAMPLE 6

Determination of the Treatment Period of a Style-Specific RNase Inhibitor and Investigation of the Fruition Rate in Fuji Apple <6-1> Determination of the Treatment Period of a Style-Specific RNase Inhibitor To test the effect of a style-specific RNase inhibitor of the present invention in a practical cultivating environment, the style-specific RNase of the present invention was treated to Fuji apple that was cultivated in a greenhouse for research (located in Cheongsong-gun, Kyungsangpukdo, Republic of Korea). In the present invention, the experiment was performed under the environmental condition that can keep the Fuji apple, a representative plant having gametophytic self-incompatibility, a single species genetically.

To determine the treatment period of a style-specific RNase inhibitor, the inhibitor was treated at the early blooming period (budding formation period~prior to full blooming), the middle blooming period (full blooming) and the late blooming period (1 day after full blooming~falling period of petal) respectively. A composition, which was manufactured by mixing the spreader of siloxane class (brand name: silhouette, Dongbu precision chemical company, Korea) with the inhibitor to the concentration of 0.0335%, was treated under the same condition of the Example 5-1, and the results were shown in Table 5.

TABLE 5

Fruition rate of Fuji apple treated with a style-specific RNase inhibitor, according to each blooming period

| Blooming period | Fruition rate of 1 mM $ZnSO_4$ treatment | Fruition rate of 1 mM $CuSO_4$ treatment |
|---|---|---|
| The early period | | |
| 5 days before blooming | >92% | >91% |
| 4 days before blooming | >93% | >86% |
| 3 days before blooming | >71% | >70% |
| 2 days before blooming | >32% | >24% |
| 1 day before blooming | 0 | 0 |
| The middle period | | |
| Full blooming | 0 | 0 |
| The late period | | |
| 1 day after full blooming | 0 | 0 |
| 2 days after full blooming | 0 | 0 |

As shown in the Table 5, the fruition rate of Fuji apple was over 70% like wild-type tomato when the composition, which is mixed with the style-specific RNase of the present invention and a spreader, was treated to it at the early blooming period (3 days~5 days before full blooming).

<6-2> Investigation of the Fruition Rate and Harmful Effect of a Medicine According to the Concentration Variation of a Style-Specific RNase Inhibitor To investigate the fruition rate and harmful effect of a medicine according to the concentration of style-specific RNase inhibitors, $ZnSO_4$ and $CuSO_4$, style-specific RNase inhibitors of the present invention, were treated to Fuji apple with various concentration in 4 days before full blooming.

Furthermore, to maximize the efficiency of the style-specific RNase inhibitor of the present invention as fruition control agents, $ZnSO_4$ or $CuSO_4$ was mixed with the spreader of siloxane class (brand name silhouette, Dongbu precision chemical company, Korea) at 0.0335%, and treated to the Fuji apple.

TABLE 6

Investigation of fruition rate and harmful effects of a medicine to Fuji apple according to the concentration variation of a style-specific RNase inhibitor

| | Effective component | | | |
|---|---|---|---|---|
| | Fruition rate and harmful effects of medicine according to the concentration variation of $ZnSO_4$ | | Fruition rate and harmful effects of medicine according to the concentration variation of $CuSO_4$ | |
| Concentration (ppm) | Fruition rate (%) | Harmful effects of a medicine | Fruition rate (%) | Harmful effects of a medicine |
| 0 | 0 | no | 0 | no |
| 20 | 0 | no | 0 | no |
| 40 | 5 | no | 0 | no |
| 60 | 17 | no | 11 | no |
| 80 | 36 | no | 39 | no |
| 100 | 72 | no | 70 | no |
| 200 | 79 | no | 76 | no |
| 300 | 93 | no | 88 | no |
| 400 | 88 | no | 85 | no |
| 500 | 85 | no | 77 | no |
| 600 | 84 | no | 73 | no |
| 700 | 74 | no | 73 | no |
| 800 | 70 | no | 52 | Weak |
| 900 | 44 | Little | 31 | Little |
| 1000 | 27 | Little | 21 | Little |
| 1100 | 9 | Little | 11 | Little |
| 1200 | 0 | Little | 0 | Little |
| 1300 | 0 | Little | 0 | Excessive |
| 1400 | 0 | Excessive | 0 | Excessive |
| 1500 | 0 | Excessive | 0 | Excessive |

As shown in Table 6, in case of $ZnSO_4$, the fruition rate by self-pollen was achieved over 70% in the range of 100~800 ppm, while harmful effect of a medicine occurred, like the colors of flower petal changed to yellow or the flower petal fell an early stage, in the concentration of 900 ppm over. In case of $CuSO_4$, the fruition rate by self-pollen was achieved over 70% in the range of 100~700 ppm, while harmful effect of a medicine also occurred in the concentration of 800 ppm over.

The experimental results of 4 times repeated experiments for 25 blooming periods were showed as the statistical value.

From the results of the Example 5 and 6, it was proven that the style-specific RNase inhibitor of the present invention could destroy the gametophytic self-incompatibility of gametophytic self-incompatible plants irrespective of species.

INDUSTRIAL APPLICABILITY

As shown in the above results, gametophytic self incompatibility was destroyed by treating with sulfates, especially $CuSO_4$ and $ZnSO_4$, the style-specific RNase inhibitor of the present invention, at the early blooming period (budding formation period~prior to full blooming), and the pollination and fruition by self-pollen was induced stably. Therefore, the fruit and plant pollinated by self-pollen can be obtained by treating a composition, which comprises a style-specific RNase inhibitor of the present invention as a effective component, to gametophytic self-incompatible fruit tree such as apple, pear, coffee, and almond etc. with optimal concentration, not by cultivating another pollinizer. As well, the present invention provides an innovative cultivating method capable of maximizing the yield per the unit area, since high fruition rate can be achieved without assistance of pollinators.

What is claimed is:

1. A method for controlling gametophytic self-incompatibility of a plant, which comprises applying to said plant a composition for regulating gametophytic self-incompatibility, which comprises a sulfate bound with a metal ion in an amount effective for inhibiting style-specific RNase activity at a specific period between budding formation and prior to full blooming.

2. The method according to claim 1, wherein said sulfate bound with a metal ion is at least one selected from the group consisting of $CuSO_4$, $MgSO_4$, $ZnSO_4$ and $MnSO_4$.

3. The method according to claim 2, wherein $CuSO_4$ is applied in a concentration of 100~700 ppm.

4. The method according to claim 2, wherein $ZnSO_4$ is applied in a concentration of 100~800 ppm.

5. The method according to claim 1 wherein said composition further comprises a spreader.

6. The method according to claim 5, wherein said spreader is selected from the group consisting of hexaconazole, siloxane and alkylaryl polyethoxylate spreaders.

7. A plant pollinated by self-pollen and treated by the method of claim 1, wherein gametophytic self-incompatibility of said plant is inhibited.

8. The plant according to claim 7, wherein said plant is selected from the group consisting of a fruit tree, a flower tree, a medicinal plant, and a vegetable.

9. The plant according to claim 8, wherein said fruit tree is selected from an apple, pear, coffee or almond tree.

10. The plant according to claim 8, wherein said vegetable is selected from tomato, eggplant, tobacco or potato.

* * * * *